US00PP13902P39

(12) United States Plant Patent
Pieters

(10) Patent No.: US PP13,902 P3
(45) Date of Patent: Jun. 24, 2003

(54) CHRYSANTHEMUM PLANT NAMED 'GEDI ONE CEN'

(75) Inventor: Dirk Pieters, Staden (BE)

(73) Assignee: Pieters Plant Production, Bvba, Oostnieuwkerke (BE)

( * ) Notice: Subject to any disclaimer, the term of this patent is extended or adjusted under 35 U.S.C. 154(b) by 11 days.

(21) Appl. No.: 09/873,908

(22) Filed: Jun. 4, 2001

(65) Prior Publication Data

US 2002/0184683 P1 Dec. 5, 2002

(51) Int. Cl.[7] ..... A01H 5/00
(52) U.S. Cl. ..... Plt./289
(58) Field of Search ..... Plt./289, 287, 290

(56) References Cited

U.S. PATENT DOCUMENTS

PP10,216 P 1/1998 Pieters ..... Plt./290
PP10,219 P 1/1998 Pieters ..... Plt./296

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, and compact growth habit.

1 Drawing Sheet

LATIN NAME

*Dendranthema morifolium*

VARIETY

'GEDI ONE CEN'

BACKGROUND OF THE INVENTION

Figure 1:
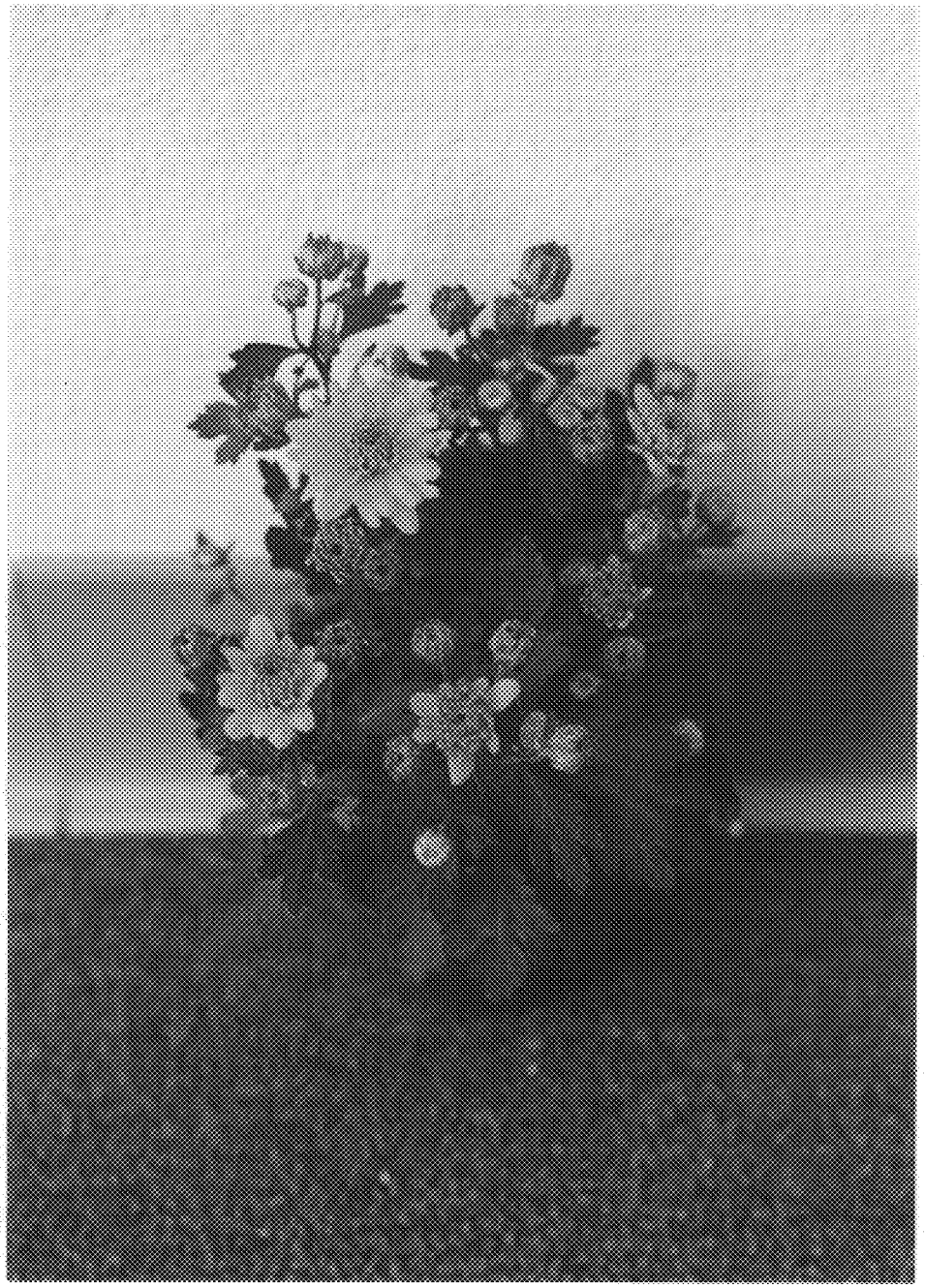

The present invention relates to a new and distinct cultivar of Chrysanthemum plant, herein after referred to by the cultivar name 'GEDI ONE CEN.'

This new cultivar originated from hybridization of a female parent, cultivar 'Bronia' (unpatented in the United States), and a male parent, cultivar 'Cobra' (U.S. Plant Pat. No. 10,219). The new cultivar was discovered by the inventor in October 1996.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE CEN' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE CEN.' These characteristics in combination distinguish 'GEDI ONE CEN' as a new and distinct Chrysanthemum:

1. Decorative type inflorescence;
2. Consistent flowering response to short days, blooming consistently after 49 days of short day length;
3. Free branching habit; and 4. Compact growth habit.

Plants of the new cultivar are similar to plants of the parent cultivar, 'Bronia,' in most horticultural characteristics, however plants of the new cultivar differed from plants of the cultivar 'Bronia' in the following characteristics:

1. The new cultivar naturally blooms 2 weeks earlier;
2. The new cultivar has blooms more uniformly; and
3. The new cultivar has more blooms per flowering branch.

Plants of the new cultivar are also similar to plants of the parent cultivar, 'Cobra,' in most horticultural characteristics, however plants of the new cultivar differed from plants of the cultivar 'Cobra' in the following characteristics:

1. The new cultivar has different ray floret color;
2. The new cultivar has a different flower type;
3. The new cultivar has more blooms per flowering branch; and
4. The new cultivar has a more flexible plant form.

The new cultivar can be compared to the Chrysanthemum cultivar 'Aldo' (disclosed in U.S. Plant Pat. No. 10,216). However plants of the new Chrysanthemum differed from the plants of the cultivar 'Aldo' in the following characteristics:

1. New cultivar has more ray florets;
2. New cultivar has a more round plant shape and greater branching;
3. New cultivar has a shorter internode length; and
4. New cultivar has a more flexible plant form.

BRIEF DESCRIPTION OF THE PHOTOGRAPHS

The photograph shows a plant of 'GEDI ONE CEN' grown in a 4-inch container. A single cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The age of the plant described herein is approximately 50 days from a rooted cutting. The growing conditions range from 60° to 65° F. at night to 70° to 85° during the day. Measurements and numerical values represent averages of typical flowering types.

Botanical classification: *Dendranthema morifolium* cultivar 'GEDI ONE CEN'.
Commercial classification: Garden-type Chrysanthemum.
Parentage: Hybridization of female parent 'Bronia' (unpatented in the United States) and male parent 'Cobra' (U.S. Plant Pat. No. 10,219).

PROPAGATION

Time to rooting: 7 to 14 days at approximately 21° C.
Root description: Fine, fibrous.

PLANT

Growth habit: Mounding herbaceous perennial.
Height: Approximately 14.7 cm.
Growth rate: Moderate.
Plant spread: Approximately 12 cm.
Branching characteristics: Free Branching.
Length of lateral branches: Approximately 10 cm.
Number of leaves per lateral branch: Approximately 7.
Internode length: Approximately 1 cm.

FOLIAGE

Leaf:
- *Arrangement.*—Alternate, single.
- *Average length.*—Approximately 3.9 cm.
- *Average width.*—Approximately 2.5 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 147A young foliage under side: Near 147A mature foliage upper side: Near 147B mature foliage under side: Near 147B venation upper side: Near 147A venation under side: Near 147B.

Petiole:
- *Average length.*—Approximately 2.5 cm.
- *Average diameter.*—0.2 cm.
- *Color.*—Approximately 137C.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last week of September.
- *Number of inflorescences per stem.*—Approximately 7.
- *Inflorescence diameter.*—Approximately 3.5 cm.
- *Inflorescence depth.*—Approximately 1 cm.
- *Inflorescence longevity on plant.*—Approximately 26–29 days.
- *Persistence.*—Persistent.
- *Inflorescence fragrance.*—Not present.

Ray florets:
- *Texture.*—Shiny.
- *Average number per inflorescence.*—Approximately 154.
- *Shape.*—Oblanceolate.
- *Margin.*—Entire.
- *Apex.*—Obtuse.
- *Length.*—Approximately 1.4 cm.
- *Width.*—Approximately 0.5 cm.
- *Color.*—Upper surface at first opening: Near 15A upper surface at maturity: Near 12A upper surface at fading: Near 12A under surface at first opening: Near 15B under surface at maturity: Near 12B under surface at fading: Near 12B.

Disc florets:
- *Appearance.*—Shiny.
- *Texture.*—Smooth.
- *Average number per inflorescence.*—Approximately 15.
- *Shape.*—Cylindric.
- *Apex.*—Obtuse.
- *Average length.*—Approximately 0.3 cm.
- *Average width.*—Approximately 0.1 cm.
- *Color.*—At first opening: Near 7A at maturity: Near 7B at fading: Near 7C.

Peduncle:
- *Length.*—At terminal end (shortest): Approximately 2.4 cm at lateral end (longest): Approximately 4.2 cm.
- *Diameter.*—Approximately 0.3 cm.
- *Surface texture.*—Lightly pubescent.
- *Strength.*—Moderate.
- *Color.*—Near 147B.
- *Habit.*—Erect.

Inflorescence bud:
- *Length.*—Approximately 0.9 cm.
- *Diameter.*—Approximately 0.6 cm.
- *Form.*—Globular.
- *Color.*—Near 167A.

Phyllaries:
- *Appearance.*—Matte.
- *Texture.*—Lightly pubescent.
- *Number.*—Approximately 40.
- *Shape.*—Ovate.
- *Margin.*—Entire.
- *Apex.*—Acute.
- *Diameter.*—Approximately 0.2 cm.
- *Length.*—Approximately 0.3 cm.
- *Color.*—Upper side: Near 137A under side: Near 137C.

REPRODUCTIVE ORGANS

Ray florets:
- *Number of pistils per flower.*—1.
- *Stigma shape.*—2 branched.
- *Stigma color.*—Near 7A.
- *Style color.*—Near 154C.
- *Style length.*—Approximately 0.4 cm.
- *Stamens.*—Absent.

Disc florets:
- *Number of pistils per flower.*—1.
- *Stigma shape.*—Cylindric.
- *Stigma color.*—Near 17A.
- *Style color.*—Near 2D.
- *Style length.*—Approximately 0.3 cm.
- *Number of stamens per flower.*—Approximately 5.

*Anther shape.*—Tubular.
*Anther color.*—Near 15C.
*Pollen color.*—Near 16A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'GEDI ONE CEN' as herein illustrated and described.

* * * * *